(12) United States Patent
Richardson

(10) Patent No.: US 7,790,698 B2
(45) Date of Patent: *Sep. 7, 2010

(54) USE OF ADENOSINE RECEPTOR AGONISTS IN THERAPY

(75) Inventor: Peter Richardson, Cambridge (GB)

(73) Assignee: Cambridge Biotechnology Ltd (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/547,454

(22) PCT Filed: Mar. 5, 2004

(86) PCT No.: PCT/GB2004/000952

§ 371 (c)(1),
(2), (4) Date: Jun. 28, 2006

(87) PCT Pub. No.: WO2004/078184

PCT Pub. Date: Sep. 16, 2004

(65) Prior Publication Data

US 2006/0234975 A1    Oct. 19, 2006

(30) Foreign Application Priority Data

Mar. 7, 2003    (GB) ................... 0305150.5

(51) Int. Cl.
*A61K 31/70* (2006.01)
*C07H 19/167* (2006.01)
(52) U.S. Cl. ...................... 514/46; 536/27.63
(58) Field of Classification Search ............ 514/46; 536/27.63
See application file for complete search history.

(56) References Cited

U.S. PATENT DOCUMENTS

| | | | |
|---|---|---|---|
| 3,936,439 A | 2/1976 | Marumoto et al. | |
| 4,225,591 A | 9/1980 | Marumoto et al. | |
| 4,255,565 A | 3/1981 | Marumoto et al. | |
| 4,705,758 A | 11/1987 | Bruns | |
| 5,104,859 A | 4/1992 | Sollevi | |
| 5,677,290 A * | 10/1997 | Fukunaga | 514/46 |
| 5,679,649 A | 10/1997 | Fukunaga | |
| 5,679,650 A * | 10/1997 | Fukunaga et al. | 514/46 |
| 5,683,989 A * | 11/1997 | Lau et al. | 514/46 |
| 5,731,296 A | 3/1998 | Sollevi | |
| 5,877,180 A | 3/1999 | Linden et al. | |
| 5,942,497 A * | 8/1999 | Fukunaga et al. | 514/46 |
| 6,004,945 A | 12/1999 | Fukunaga | |
| 6,180,616 B1 | 1/2001 | Fukunaga | |
| 6,642,209 B1 | 11/2003 | Fukunaga | |

FOREIGN PATENT DOCUMENTS

| | | |
|---|---|---|
| AU | 49412/72 | 5/1974 |
| DE | 2258378 | 6/1973 |
| FR | 2162128 | 7/1973 |
| WO | WO 9638728 | 12/1996 |
| WO | WO99/34804 | 7/1999 |
| WO | WO 2004079329 | 9/2004 |

OTHER PUBLICATIONS

Ueeda et al., "Cardiovascular Actions of Adenosines, But Not Adenosine Receptors, Differ in Rat and Guinea Pig," Life Sciences, 49(18), 1351-1358 (1991).*

Makujina et al., "Structure-Activity Relationship of 2-(ar)alkoxyadenosines at the Adenosine Receptor in Coronary Artery," European Journal of Pharmacology, 243(1), 35-38 (1993).*

Makujina et al., "Structure-Activity Relationship of 2-(ar)alkoxyadenosines at the Adenosine Receptor in Coronary Artery," European Journal of Pharmacology, 243(1), 35-38 (1993).*

Herrick-Davis et al., "Evaluation of Adenosine Agonists as Potential Analgesics," European Journal of Pharmacology, 162(2), 365-369 (Mar. 21, 1989).*

Karlsten et al., "The Antinociceptive Effect of Intrathecally Administered Adenosine Analogs in Mice Correlates with the Affinity for the A1-Adenosine Receptor," Neuroscience Letters, 121(1-2), 267-270 (Jan. 2, 1991).*

Venes et al.(eds.), Taber's Cyclopedic Medical Dictionary, 19th Edition, F. A. Davis Co., Philadelphia, PA, 2001, see pp. 1092-1094 (definition of "inflammation" at col. 1 of p. 1092).*

Bartlett, R.T., et al., "Synthesis and Pharmacological Evaluation of a Series of Analogues of 1-methylisoquanosine," Journal of Medicinal Chemistry, American Chemical Society, vol. 24, 1981, pp. 947-954.

(Continued)

*Primary Examiner*—Lawrence E Crane
(74) *Attorney, Agent, or Firm*—Fish & Richardson P.C.

(57) ABSTRACT

Compounds of the class of adenosines, represented by structural formula I, wherein R is $C_{1-4}$ alkoxy, and X is H or OH, are useful in a method of preventing, treating, or ameliorating various conditions or disorders, e.g., inflammation, which comprises administering a compound of formula I to a subject in need of such prevention, treatment, or amelioration, for example, at a dosage which gives rise to a peak plasma concentration in the subject that is less than the EC50 value of the compound at adenosine receptors at nH 7.4.

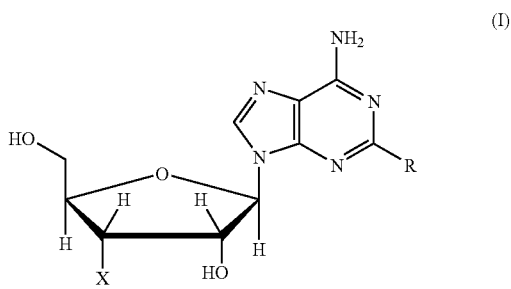

(I)

14 Claims, 3 Drawing Sheets

OTHER PUBLICATIONS

Belardinelli, L. et al., "Isolated atrial myocytes: adenosine and acetylcholine increase potassium conductance," G Am. J. Physiol. 224, H734-H737.

Klitgaard et al., "Contrasting effects of adenosine $A_1$ and $A_2$ receptor ligands in different chemoconvulsive rodent models," Eur J. Pharmacol. (1993) 242,221-228.

Knabb et al., "Consistent Parallel Relationships among Myocardial Oxygen Consumption, Coronary Blood Flow, and Pericardial Infusate Adenosine Concentration with Various Interventions and β-Blockade in the Dog," Circ. Res. (1983) 53, 33-41.

Rieger, J.M., et al., "Design, Synthesis, and Evaluation of Novel A2A Adenosine Receptor Agonists," Journal of Medicinal Chemistry, American Chemical Society, vol. 44, 2001, pp. 531-539.

Sawynok, J., "Adenosine receptor activation and nociception," Eur J. Pharmacol. (1998) 317, 1-11.

Ueeda, M., et al., "2-Alkoxyadenosines: Potent and Selective Agonists at the Coronary Artery A2 Adenosine Receptor," Journal of Medicinal Chemistry, American Chemical Society, vol. 34, 1991, pp. 1334-1339.

"Aldrich Handbook of Fine Chemicals and Laboratory Equipment," 1015-1016, (2000); XP002366927.

Askalan, R. et al., "Role of Histidine Residues in the Adenosine A2A Receptor Ligand Binding Site," *Journal of Neurochemistry*, 63(4):1477-84, (1994); XP001196996.

Belfrage, M. et al., "The Safety and Efficacy of Intrathecal Adenosine in Patients with Chronic Neuropathic Pain," *Anesthesia and Analgesia*, 89(1):136-42, (1999); XP009027670.

Bhakuni, D., "Biological Activity of Marine Nucleosides and their Analogues," *Proceedings of the Indian National Science Academy*. Part B Biological Sciences, 65(Part 2):97-112, (1995); XP001165752.

Bressi, J. et. al., "Adenosine Analogues as Inhibitors of *Trypanosoma brucei* Phosphoglycerate Kinase: Elucidation of a Novel Binding Mode for a 2-Amino-N6-Substituted Adenosine," *Journal of Medicinal Chemistry*, 43(22):4135-50, (2000); XP000999137.

Collins, S. et al., "The Effect of GR190178, a Selective Low-Efficacy Adenosine A1 Receptor Agonist, on the Treatment of Neuropathic Hyperalgesia in the Rat," *British Journal of Pharmacology*, 133(Proceedings Supplement):48p (2001), Proceedings of the British Pharmacological Society Meeting, (Dec. 18-21, 2000); XP009027671.

Daly, J. et al., "Structure-Activity Relationships for N6-Substituted Adenosines at a Brain A1-Adenosine Receptor with a Comparison to an A2-Adenosine Receptor Regulating Coronary Blood Flow," *Biochemical Pharmacology*, 35(15):2467-81 (1986) XP009010090.

Dan, K., "Nerve Block Therapy and Postherpetic Neuralgia," *Critical Reviews in Physical and Rehabilitation Medicine*, 7(2):93-112 (1995) Embase Database Accession No. EMB-1995373280. XP002273335.

De Zwart, M. et al., "5'-N-Substituted Carboxamidoadenosines as Agonists for Adenosine Receptors," *Journal of Medicinal Chemistry*, 42(8): 1384-92 (1999) XP001002032.

Deghati, P. et al., "Regioselective Nitration of Purine Nucleosides: Synthesis of 2-Nitroadenosine and 2-Nitroinosine," *Tetrahedron Letters*, 41(8):1291-5 (2000) XP004188609.

Feoktistov, I. et al., "Adenosine A2B Receptors: A Novel Therapeutic Target in Asthma?," *Trends in Pharmacological Sciences*, 19(4):148-53 (1998) XP002287445.

Fishman, P. et al., "A3 Adenosine Receptor as a Target for Cancer Therapy," *Anti-Cancer Drugs*, 13(5):437-43 (2002) XP009024520.

Hiley, C. et al., "Effects of pH on Responses to Adenosine, CGS 21680, Carbachol and Nitroprusside in the Isolated Perfused Superior Mesenteric Arterial Bed of the Rat," *British Journal of Pharmacology*, 116(6):2641-6 (1995) XP008032448.

Jiang, Q. et al., "Mutagenesis Reveals Structure-Activity Parallels Between Human A2A Adenosine Recveptors and Biogenic Amine G Protein-Coupled Receptors," *Journal of Medicinal Chemistry*, 40(16):2588-95 (1997) XP002287314.

Kaul, P. et al., "Adenosine Agonist of Marine Origin Indicative of Two Types of Adenosinergic Receptors," *Pharmacologist*, 23(3):540 (1981) XP009027638.

Keeling, S. et al., "The Discovery and Synthesis of Highly Potent, A2a Receptor Agonists," *Bioorganic and Medicinal Chemistry Letters*, 10(4):403-6 (2000) XP004189943.

Kirk, I. et al., "Further Characterization of [3H]-CGS 21680 Binding Sites in the Rat Striatum and Cortex," *British Journal of Pharmacology*, 114(2):537-43 (1995) XP008032472.

Klitgaard, H. et al., "Contrasting Effects of Adenosine $A_1$ and $A_2$ Receptor Ligands in Different Chemoconclusive Rodent Models," *European Journal of Pharmacology*, 242:221-8 (1993).

König, G., "Meeresorganismen als Quelle Pharmazeutisch Bedeutsamer Naturstoffe," *Deutsche Apotheker Zeitung*, 132(14):673-83 (1992) XP002255617.

Marumoto, R. et al. "Synthesis and Coronary Vasodilating Activity of 2-Substituted Adenosines," *Chemical and Pharmaceutical Bulletin*, 23(4):759-74 (1975) XP002154408.

Matova, M. et al. "QSAR Analysis of 2-Alkyloxy and 2-Aralkyloxy Adenosine A1- and A2-Agonists," *European Journal of Medicinal Chemistry*, 32(6):505-13 (1997) XP004088461.

Matsuda et al., Nucleosides and Nucleotides. XXVII. Synthesis of 2- and 8-Cyanoadenosines and their Derivatives, *Chemical and Pharmaceutical Bulletin*, 27(1):183-92 (1979) XP002127436.

Matsuda, A. et al., "Nucleosides and Nucleotides. 103. 2-Alkyladenosines: a Novel Class of Selective Adenosine A2 Receptor Agonists with Potent Antihypertensive Effects," *Journal of Medicinal Chemistry*, 35:241-52 (1992) XP002170995.

Miles, R. et al., "Nucleic Acid Related Compounds," *Journal of the American Chemical Society*, 117:5951-7 (1995) XP002366161.

Nair, V. et al., "Novel, Stable Cogeners of the Antiretroviral Compound 2', 3'-Dideoxyadenosine," *Journal of the American Chemical Society*, 111(22):8502-4 (1989) XP001105896.

Ojha, L. et al., "A Simple Method for Synthesis of Spongosine, Azaspongosine, and their Antiplatelet Effects," *Nucleosides and Nucleotiodes*, 14(9-10):1889-1900 (1995) XP009027643.

Okusa, M., "A2A Adenosine Receptor: A Novel Therapeutic Target in Renal Disease," *American Journal of Physiology*, 282(1 Part 2):F10-F18 (2002) XP002287448.

Ribeiro, J. et al., "Adenosine Receptors in the Nervous System: Pathophysiological Implications," *Progress in Neurobiology*, 68(6):377-92 (2002) XP002287447.

Schaeffer, H. et al., "Synthesis of Potential Anticancer Agents. XIV. Ribosides of 2, 6-Disubstituted Purines," *Journal of the American Chemical Society*, 80:3738-42 (1958) XP002300926.

Smith, J. et al., "The Effects of Reduced pH on A2B Adenosine Receptor-Evoked Cyclic AMP Generation in the Guinea-Pig Cerebral Cortex," *British Journal of Pharmacology*, 123 (Proc. Suppl.): 195p (1998). Meeting of the British Pharmacological Society Held Jointly with the Dutch Pharmacological Society (Dec. 10-12, 1997) XP008032489.

Sullivan, G. et al., "Role of A2A Adenosine Receptors in Inflammation," *Drug Development Research*, 45(3/4):103-12 (1998) XP000978332.

Ueeda, M. et al., "2-Aralkoxyadenosines: Potent and Selective Agonists at the Coronary Artery A2 Adenosine Receptor," *Journal of Medicinal Chemistry*, 34(4):1340-1344 (1991) XP004088461.

Umino, T. et al., "Nucleosides and Nucleotides. 200. Reinvestigation of 5'-N-Ethylcarboxamidoadenosine Derivatives: Structure-Activity Relationships for P(3) Purinoceptor-Like Proteins," *Journal of Medicinal Chemistry*, 44:208-14 (2001) XP002366162.

Vittori, S. et al., "2-Alkenyl and 2-Alkyl Derivatives of Adenosine and Adenosine-5'-N-Ethyluronamide: Different Affinity and Selectivity of E- and Z-Diastereomers at A2A Adenosine Receptors," *Journal of Medicinal Chemistry*, 39:4211-7 (1996) XP002366163.

International Preliminary Report on Patentability for Application No. PCT/GB2004/000952, dated Aug. 25, 2005.

International Search Report for PCT/GB2004/000952,- dated Aug. 25, 2005.

Ali Akbar Nekooeian et al., "Effects of adenosine $a_{2a}$ receptor agonist, cgs 21680, on blood pressure, cardiac index and arterial conductance in anaesthetized rats", 1996, European Journal of Pharmacology, vol. 307, pp. 163-169.

R.A.A. Mathôt et al., "Pharmacokinetic-haemodynamic relationships of 2-chloroadenosine at adenosine $A_1$ and $A_{2a}$ receptors in vivo", 1996, British Journal of Pharmacology, vol. 118, No. 2, pp. 369-377.

John R. Keddie et al., "In vivo characterisation of ZM 241385, a selective adenosine $A_{2a}$ receptor antagonist", 1996, European Journal of Pharmacology, vol. 301, pp. 107-113.

Randy L. Webb et al., "Development of Tolerance to the Antihypertensive Effects of Highly Selective Adenosine $A_{2a}$ Agonists upon Chronic Administration", 1993, The Journal of Pharmacology and Experimental Therapeutics, vol. 267, pp. 287-295.

R.L. Webb et al., "Cardiovascular Effects of Adenosine $A_2$ Agonists in the Conscious Spontaneously Hypertensive Rat: A Comparative Study of Three Structurally Distinct Ligands", 1991, The Journal of Pharmacology and Experimental Therapeutics, vol. 259, pp. 1203-1212.

C. Casati et al., "Telemetry Monitoring of Hemodynamic Effects Induced Over Time by Adenosine Agonists in Spontaneously Hypertensive Rats", 1995, The Journal of Pharmacology and Experimental Therapeutics, Vo. 275, pp. 914-919.

Erminio Bonizzoni et al., "Modeling Hemodynamic Profiles by Telemetry in the Rat, A Study With $A_1$ and $A_{2a}$ Adenosine Agonists", 1995, Hypertension, vol. 25, No. 4, Part 1, pp. 564-569.

Cristina Alberti et al., "Mechanism and Pressor Relevance of the Short-Term Cardiovascular and Renin Excitatory Actions of the Selective $A_{2a}$-Adenosine Receptor Agonists", 1997, Journal of Cardiovascular Pharmacology, vol. 30, No. 1, pp. 320-324.

* cited by examiner

A)

B)

USE OF ADENOSINE RECEPTOR AGONISTS IN THERAPY

CROSS REFERENCE TO RELATED APPLICATIONS

This application is a national phase filing under 35 U.S.C. §371 of international application number PCT/GB2004/000952, filed Mar. 5, 2004, which claims the benefit of priority of British application number 0305150.5, filed Mar. 7, 2003. The disclosures of the prior applications are considered part of (and are incorporated by reference in) the disclosure of this application.

TECHNICAL FIELD

This invention relates to use of adenosine receptor agonists as therapeutic compounds.

BACKGROUND

Adenosine is a ubiquitous local hormone/neurotransmitter that acts on four known receptors, the adenosine A1, A2A, A2B and A3 receptors. Adenosine generally serves to balance the supply and demand of energy in tissues. For example, in the heart released adenosine slows the heart by an A1 receptor mediated action in the nodes and atria (Belardinelli, L & Isenberg, G Am. J. Physiol. 224, H734-H737), while simultaneously dilating the coronary artery to increase energy (i.e. glucose, fat and oxygen) supply (Knabb et al., Circ. Res. (1983) 53, 33-41). Similarly, during inflammation adenosine serves to inhibit inflammatory activity, while in conditions of excessive nerve activity (e.g. epilepsy) adenosine inhibits nerve firing (Klitgaard et al., Eur J. Pharmacol. (1993) 242, 221-228). This system, or a variant on it, is present in all tissues.

Adenosine itself can be used to diagnose and treat supraventricular tachycardia. Adenosine A1 receptor agonists are known to act as powerful analgesics (Sawynok, J. Eur J Pharmacol. (1998) 347, 1-11). Adenosine A2A receptor agonists are known to act as anti-inflammatory agents (for example, from U.S. Pat. No. 5,877,180 and WO 99/34804). In experimental animals, A2A receptor agonists have been shown to be effective against a wide variety of conditions including sepsis, arthritis, and ischaemia/reperfusion injury arising from renal, coronary or cerebral artery occlusion. The common factor in these conditions is a reduction in the inflammatory response caused by the inhibitory effect of this receptor on most, if not all, inflammatory cells.

However, the ubiquitous distribution of adenosine receptors means that administration of adenosine receptor agonists causes adverse side effects. This has generally precluded the development of adenosine-based therapies. Selective A1 receptor agonists cause bradycardia. The first selective A2A receptor agonist (2-[4-(2-carboxyethyl)phenylethylamino]-5'-N-ethylcarboxamidoadenosine, or CGS21680), was tested in a Phase 2A clinical trial as a potential anti-hypertensive. However, administration caused a large fall in blood pressure and consequent increase in cardiac output. FR 2162128 discloses that adenosine derivatives (including 2-alkoxy adenosine derivatives comprising a lower alkyl group of not less than two carbon atoms) have hypotensive and coronary vasodilatory activity.

Bartlett et al (J. Med. Chem. 1981, 24, 947-954) discloses the evaluation of analogues of 1-methylisoguanosine. These analogues include 2-methoxyadenosine (also known as spongosine). This and other compounds were tested for their skeletal muscle-relaxant, hypothermic, cardiovascular and anti-inflammatory effects in rodents following oral administration (anti-inflammatory activity was assessed by inhibition of carageenan-induced oedema in a rat paw). 2-methoxyadenosine caused 25% inhibition of carageenan-induced inflammation in rats at 20 mg/kg po. However, reductions in mean blood pressure (41%), and in heart rate (25%) were also observed after administration of this compound at this dose.

SUMMARY AND DETAILED DESCRIPTION

There is, therefore, a need to provide adenosine receptor agonists that can be administered with minimal side effects.

According to the invention there is provided use of a compound of the following formula:

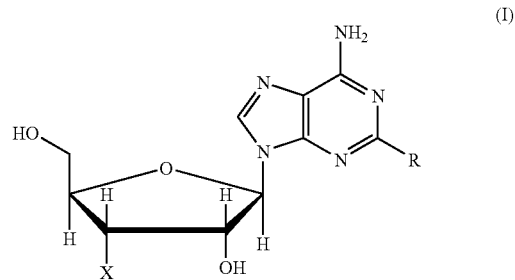

wherein R is $C_{1-4}$ alkoxy and X is OH;

for the manufacture of a medicament for the prevention, treatment, or amelioration of cancer, inflammation, auto-immune disease, ischemia-reperfusion injury, epilepsy, sepsis, septic shock, neurodegeneration (including Alzheimer's Disease), muscle fatigue or muscle cramp (particularly athletes' cramp).

According to the invention there is also provided use of a compound of the following formula:

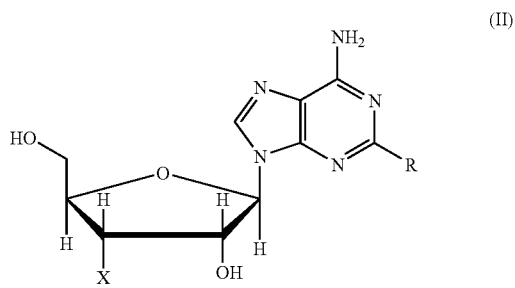

wherein R is $C_{1-4}$ alkoxy, and X is H;

for the manufacture of a medicament for the prevention, treatment, or amelioration of cancer, inflammation, auto-immune disease, ischemia-reperfusion injury, epilepsy, sepsis, septic shock, neurodegeneration (including Alzheimer's Disease), muscle fatigue or muscle cramp (particularly athletes' cramp).

In particular, there is provided according to the invention use of a compound of formula I or II for the manufacture of a medicament for the prevention, treatment, or amelioration of inflammatory or auto-immune disease, including rheumatoid arthritis, osteoarthritis, rheumatoid spondylitis, gouty arthritis, and other arthritic conditions, psoriasis, asthma, chronic obstructive pulmonary disease, fibrosis, multiple sclerosis, endotoxic shock, gram negative shock, toxic shock, hemorrhagic shock, adult respiratory distress syndrome, cerebral malaria TNF-enhanced HIV replication, TNF inhibition of AZT and DDI activity, organ transplant rejection, cachexia secondary to cancer, HIV, chronic pulmonary inflammatory disease, silicosis, pulmonary sarcosis, bone resorption diseases, reperfusion injury (including damage caused to organs as a consequence of reperfusion following ischaemic episodes e.g. myocardial infarcts, strokes), autoimmune damage (including multiple sclerosis, Guillam Barre Syndrome, myasthenia gravis) graft v. host rejection, allograft rejections, fever and myalgia due to infection, cachexia secondary to infection or malignancy, cachexia secondary to acquired immune deficiency syndrome (AIDS), AIDS related complex (ARC), keloid formation, scar tissue formation, Crohn's disease, ulcerative colitis and pyresis, irritable bowel syndrome, osteoporosis, cerebral malaria, bacterial meningitis, adverse effects from amphotericin B treatment, adverse effects from interleukin-2 treatment, adverse effects from OKT3 treatment, and adverse effects from GM-CSF treatment.

Compounds of formula (I) or (II) that are selective agonists of adenosine A2A and/or A3 receptors are particularly preferred because it is believed that such compounds will have strong anti-inflammatory activity. By selective agonists of adenosine A2A and/or A3 receptors is meant agonists that activate adenosine A2A and/or A3 receptors at concentrations that are lower (preferably one thousandth to one fifth) than required to activate adenosine A1 receptors. Furthermore, A1 receptors have pro-inflammatory activity, so such effects are expected to be minimised for compounds that are selective for A2A and/or A3 receptors.

Compounds of formula (I) include: 2-methoxyadenosine, 2-ethoxyadenosine, 2-propoxyadenosine, 2-isopropoxyadenosine, and 2-butoxyadenosine. Preferred compounds of formula (I) are 2-methoxyadenosine, 2-ethoxyadenosine, and 2-butyloxyadenosine.

Compounds of formula (II) include: 3'-deoxy-2-methoxyadenosine, 3'-deoxy-2-ethoxyadenosine, 3'-deoxy-2-propoxyadenosine, 3'-deoxy-2-isopropoxyadenosine, and 3'-deoxy-2-butoxyadenosine. Preferred compounds of formula (II) are 3'-deoxy-2-propoxyadenosine, 3'-deoxy-2-isopropoxyadenosine, and 3'-deoxy-2-butoxyadenosine.

2-methoxyadenosine has been reported to have an EC50 value at the adenosine A2A receptor of 3 μM (Daly, J. W. et al., (1993) Pharmacol. 46, 91-100). However, this compound surprisingly has profound anti-inflammatory activity at plasma concentrations of 0.2 μM or less. At these low doses 2-methoxyadenosine has reduced probability and severity of side effects. 2-methoxyadenosine can be administered at concentrations at which it is effective as an anti-inflammatory, but which are below those at which side effects are observed.

Other compounds of formula (I) and compounds of formula (II) are also believed to be much more effective at low doses than other adenosine receptor agonists. Thus, it is expected that compounds of formula (I) and compounds of formula (II) can be effectively administered at doses at which they have reduced probability and severity of side effects, or at which side effects are not observed. Such compounds provide significant advantages over the vast majority of other adenosine receptor agonists which only have anti-inflammatory effects at the same concentrations at which serious side effects are observed.

Compounds of formula (I) or (II) may alternatively or additionally have reduced probability and severity of side effects compared to other adenosine receptor agonists.

The amount of a compound of formula (I) or (II) that is administered to a subject should be an amount which gives rise to a peak plasma concentration that is less than the EC50 value of the compound at adenosine receptors at pH 7.4.

It will be appreciated that the EC50 value of the compound is likely to be different for different adenosine receptors (i.e. the A1, A2A, A2B, A3 adenosine receptors). The amount of the compound that is to be administered should be calculated relative to the lowest EC50 value of the compound at the different receptors.

Preferably the peak plasma concentration is one thousandth to one fifth, or one fiftieth to one third (more preferably one thousandth to one twentieth, one hundredth or one fiftieth to one fifth, one fiftieth to one tenth, or one tenth to one fifth) of the EC50 value. Preferably the amount administered gives rise to a plasma concentration that is maintained for more than one hour between one thousandth and one fifth, more preferably between one thousandth and one twentieth, or one hundredth and one fifth, or one fiftieth and one fifth, of the EC50 value of the compound at adenosine receptors at pH 7.4.

For the avoidance of doubt, the EC50 value of a compound is defined herein as the concentration of the compound that provokes a receptor response halfway between the baseline receptor response and the maximum receptor response (as determined, for example, using a dose-response curve).

The EC50 value should be determined under standard conditions (balanced salt solutions buffered to pH 7.4). For EC50 determinations using isolated membranes, cells and tissues this would be in buffered salt solution at pH 7.4 (e.g. cell culture medium), for example as in Daly et al., Pharmacol. (1993) 46, 91-100), or preferably Tilburg et al (J. Med. Chem. (2002) 45, 91-100). The EC50 could also be determined in vivo by measuring adenosine receptor mediated responses in a normal healthy animal, or even in a tissue perfused under normal conditions (i.e. oxygenated blood, or oxygenated isotonic media, also buffered at pH 7.4) in a normal healthy animal.

Alternatively, the amount of a compound of formula (I) or (II) that is administered may be an amount that results in a peak plasma concentration that is one thousandth to one twentieth, one thousandth to one third, more preferably one hundredth to one fifth, or one fiftieth to one tenth, of the Kd value at adenosine receptors.

It will be appreciated that the Kd value of the compound is likely to be different for different adenosine receptors (i.e. the A1, A2A, A2B, A3 adenosine receptors). The amount of the compound that is to be administered should be calculated relative to the lowest Kd value of the compound for the different receptors.

Preferably the amount of the compound that is administered is an amount that results in a plasma concentration that is maintained for at least one hour between one thousandth and one fifth, more preferably between one thousandth and one twentieth, or one hundredth and one fifth, or one fiftieth and one fifth, of the Kd value of the compound at adenosine receptors.

The Kd value of the compound at each receptor should be determined under standard conditions using plasma membranes as a source of the adenosine receptors derived either from tissues or cells endogenously expressing these receptors or from cells transfected with DNA vectors encoding the adenosine receptor genes. Alternatively whole cell preparations using cells expressing adenosine receptors can be used. Labelled ligands (e.g. radiolabelled) selective for the different receptors should be used in buffered (pH7.4) salt solutions (see e.g. Tilburg et al, J. Med. Chem. (2002) 45, 420-429) to determine the binding affinity and thus the Kd of the compound at each receptor.

Alternatively, the amount of a compound of formula (I) or (II) that is administered may be an amount that is one thousandth to one fifth, or one fiftieth to one third (preferably one thousandth to one twentieth, or one hundredth or one fiftieth to one fifth) of the minimum dose of the compound that gives rise to bradycardia, hypotension or tachycardia side effects in animals of the same species as the subject to which the compound is to be administered. Preferably the amount is one tenth to one fifth of the minimum dose that gives rise to the side effects. Preferably the amount administered gives rise to a plasma concentration that is maintained for more than 1 hour between one thousandth and one twentieth, or one hundredth or one fiftieth and one fifth of the minimum dose that gives rise to the side effects.

Alternatively, the amount of a compound of formula (I) or (II) that is administered may be an amount that gives rise to plasma concentrations that are one thousandth to one fifth, or one fiftieth to one third (preferably one thousandth to one twentieth, or one hundredth or one fiftieth to one fifth) of the minimum plasma concentration of the compound that cause bradycardia, hypotension or tachycardia side effects in animals of the same species as the subject to which the compound is to be administered. Preferably the amount gives rise to plasma concentrations that are one tenth to one fifth of the minimum plasma concentration that causes the side effects. Preferably the amount administered gives rise to a plasma concentration that is maintained for more than 1 hour between one thousandth and one twentieth, or one hundredth or one fiftieth and one fifth, of the minimum plasma concentration that causes the side effects.

It is expected that the amount of a compound of formula (I) or (II) that is administered should be 0.01 to 15 mg/kg, for example 0.01 to 5 or 10 mg/kg. The amount may be less than 6 mg/kg, for example 0.01 to 2 mg/kg. The amount may be at least 0.01 or 0.1 mg/kg, for example 0.1 to 2 mg/kg, or 0.2 to 1 mg/kg. A typical amount is 0.2 or 0.6 to 1.2 mg/kg.

Preferred doses for a 70 kg human subject are less than 420 mg, preferably at least 0.7 mg, more preferably at least 3.5 mg, most preferably at least 7 mg. More preferably 7 to 70 mg, or 14 to 70 mg.

The dosage amounts specified above are significantly lower (up to approximately 100 times lower) than would be expected (based on the EC50 value of spongosine at the adenosine A2A receptor) to be required for the compounds of formula (I) to have any beneficial therapeutic effect.

The appropriate dosage of a compound of formula (I) or (II) will vary with the age, sex, weight, and condition of the subject being treated, the potency of the compound, and the route of administration, etc. The appropriate dosage can readily be determined by one skilled in the art.

Compounds of formula (I) and compounds of formula (II) may be particularly effective for the prevention, treatment, or amelioration of particular types of inflammation, including arthritis (particularly at the joint capsule of arthritis), asthma, psoriasis, and bowel inflammation.

Compounds of formula (I) and compounds of formula (II) may be particularly effective in the prevention, treatment, or amelioration of rheumatoid arthritis, irritable bowel syndrome or osteoarthritis.

There is further provided according to the invention a method of prevention, treatment, or amelioration of cancer, inflammation, ischemia-reperfusion injury, epilepsy, sepsis, septic shock, neurodegeneration (including Alzheimer's Disease), muscle fatigue or muscle cramp (particularly athletes' cramp), which comprises administering a compound of formula (I) or (II) to a subject in need of such prevention, treatment, or amelioration.

Embodiments of the invention relating to use of a compound of formula (I) (particularly for the prevention, treatment, or amelioration of inflammation) may exclude 2-methoxyadenosine.

Compounds of formula (I) or (II) may be administered with or without other therapeutic agents, for example analgesics (such as opiates, NSAIDs, cannabinoids, tachykinin modulators, or bradykinin modulators) or anti-hyperalgesics (such as gabapentin, pregabalin, cannabinoids, sodium or calcium channel modulators, anti-epileptics or anti-depressants).

In general, a compound of formula (I) or (II) may be administered by known means, in any suitable formulation, by any suitable route. A compound of the invention is preferably administered orally, parenterally, sublingually, transdermally, intrathecally, or transmucosally. Other suitable routes include intravenous, intramuscular, subcutaneous, inhaled, and topical. The amount of drug administered will typically be higher when administered orally than when administered, say, intravenously.

Suitable compositions, for example for oral administration, include solid unit dose forms, and those containing liquid, e.g. for injection, such as tablets, capsules, vials and ampoules, in which the active agent is formulated, by known means, with a physiologically acceptable excipient, diluent or carrier. Suitable diluents and carriers are known, and include, for example, lactose and talc, together with appropriate binding agents etc.

A unit dosage of a compound of the invention typically comprises 5 to 500 mg of the active agent. Preferably the active agent is in the form of a pharmaceutical composition comprising the active agent and a physiologically acceptable carrier, excipient, or diluent. The preferred dosage is 0.1 to 2, e.g. 0.5 to 1, typically about 0.2 or 0.6, mg of the active agent per kg of the (human) subject. At these levels, effective treatment can be achieved substantially without a concomitant fall (for example, no more than 10%) in blood pressure.

A preferred administration frequency of compounds of the invention is expected to be two or three times per day.

Compounds of the invention can also serve as a basis for identifying more effective drugs, or drugs that have further reduced side effects.

Embodiments of the invention relating to compounds of formula (I) may exclude 2-propoxyadenosine, and/or 2-isopropoxyadenosine.

Embodiments of the invention relating to compounds of formula (II) may exclude 3'-deoxy-2-methoxyadenosine and/or 3'-deoxy-2-ethoxyadenosine.

Embodiments of the invention are described in the following examples with reference to the accompanying drawings in which:

EXAMPLES

Example 1

Figure 1:
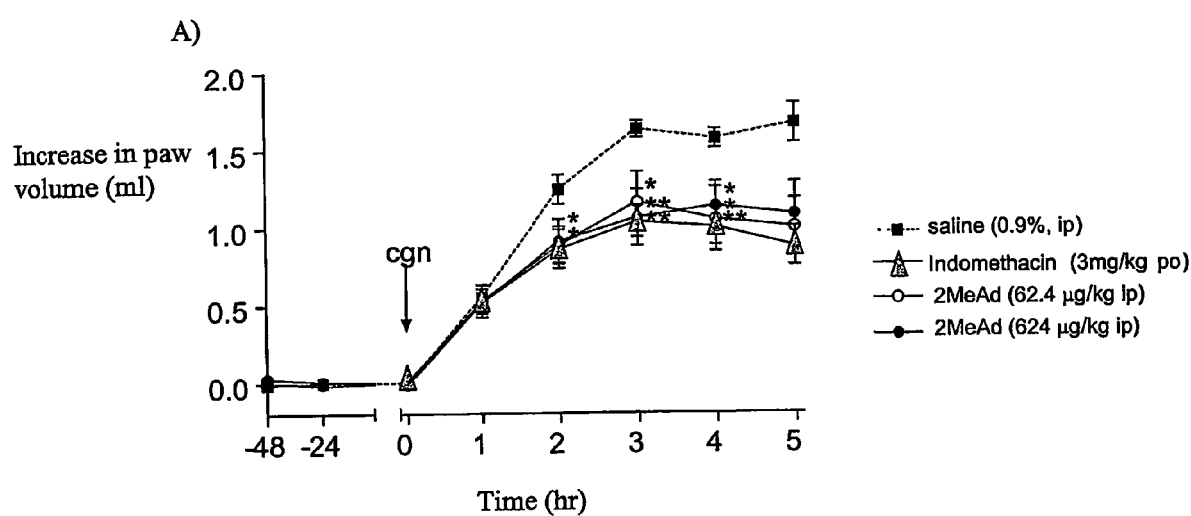
FIG. 1 shows that 2-methoxyadenosine inhibits carrageenan induced inflammation without affecting blood pressure.

FIG. 1: A. 2-methoxyadenosine (62.4 and 624 μg/kg i.p.) inhibits carrageenan (CGN) induced inflammation with comparable efficacy to indomethacin (3 mg/kg, po), without affecting blood pressure. Carrageenan (2%, 10 microlitres) was administered into the right hind paw, and the paw volume assessed by plethysomometry. 2-methoxyadenosine was administered at the same time as carrageenan. 2-methoxyadenosine was as effective as indomethacin (Indo, 3 mg/kg p.o.).

Example 2

Figure 2:
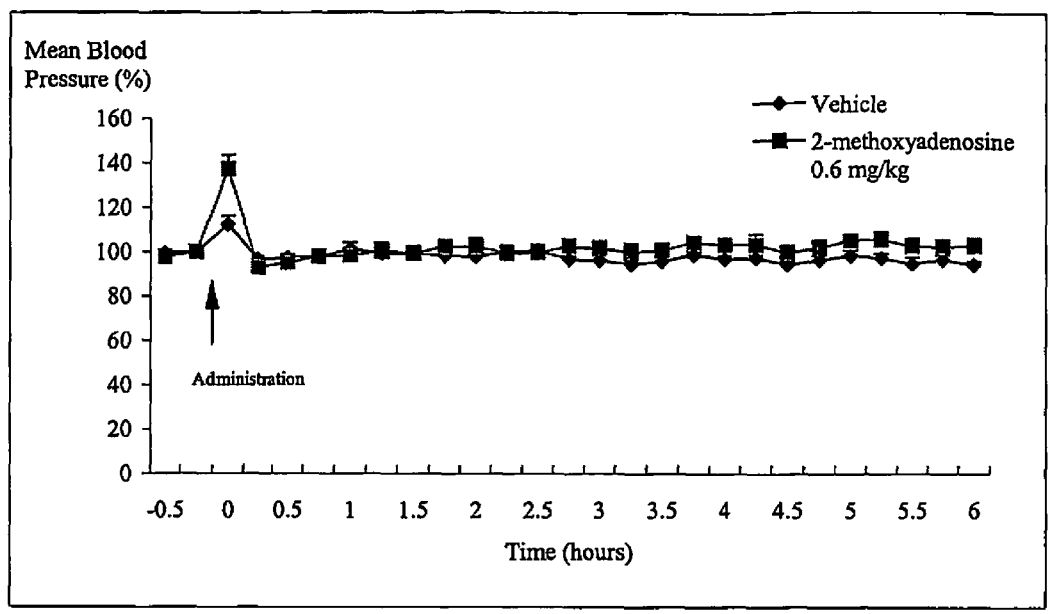
FIG. 2 shows that 2-methoxyadenosine (0.6 mg/kg p.o.) has no significant effect on blood pressure or heart rate.
Figure 2:
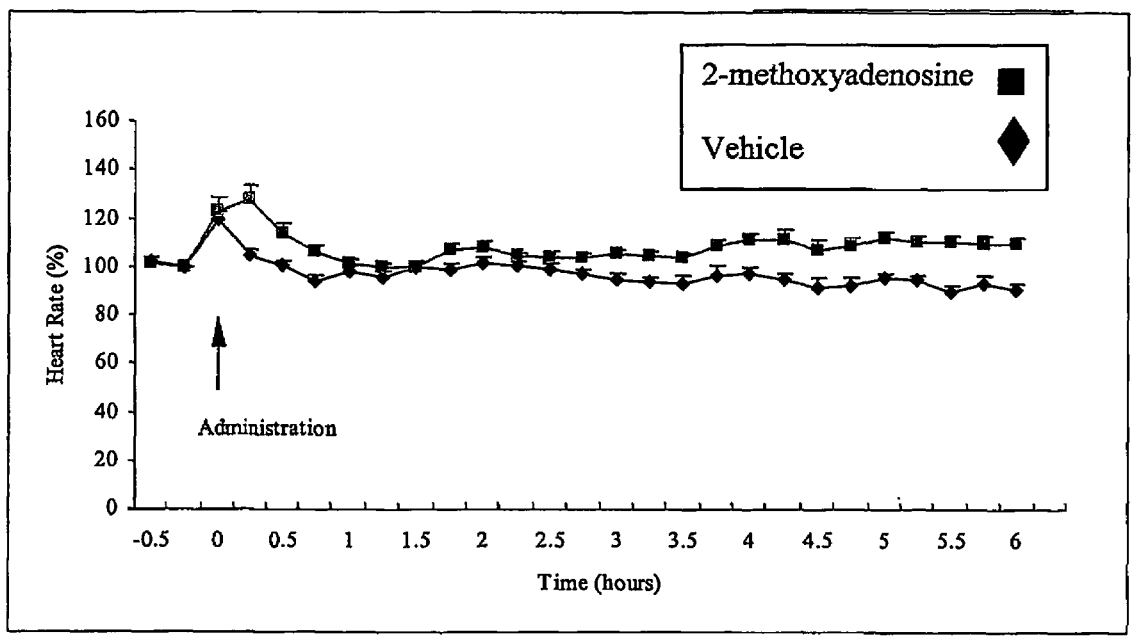

FIG. 2: An implantable radiotelemetry device was placed in the abdominal cavity of 6 rats per group. The pressure catheter of the device was inserted in the abdominal aorta and two electrodes tunnelised under the skin in a lead II position (left side of abdominal cavity/right shoulder). Individual rats were placed in their own cage on a radioreceptor (DSI) for data acquisition. The effect of 0.6 mg/kg 2-methoxyadenosine or vehicle (p.o.) on blood pressure was then assessed. A: blood pressure; B: heart rate.

Example 3

Figure 3:
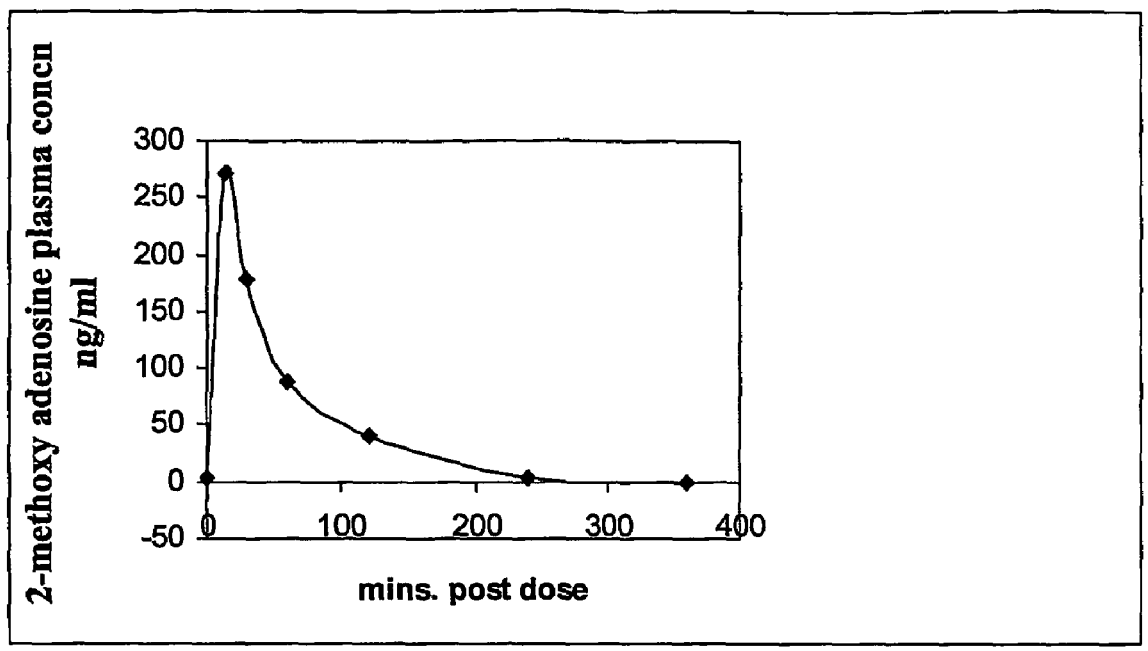
FIG. 3 shows the change in plasma concentration over time after administration of 2-methoxyadenosine.

The EC50 value of 2-methoxyadenosine at the adenosine A2A receptor is 900 ng/ml (3 μM). FIG. 3 shows the change in plasma concentration over time after administration of 2-methoxyadenosine at 0.6 mg/kg to a rat. It can be seen that the plasma concentration remains above 2% of the EC50 value for more than 3 hours. Anti-inflammatory effects have been observed (without blood pressure changes) when the peak and maintained plasma concentrations are as low 8 ng/ml (i.e. 2% of the EC50 value determined in vitro). If the peak plasma concentration reaches the 900 ng/ml level (i.e. the EC50 value) profound reductions in blood pressure occur that last for many hours.

The invention claimed is:

1. A method of treatment of inflammation, which comprises administering a compound of formula (I) or a pharmaceutically acceptable salt thereof:

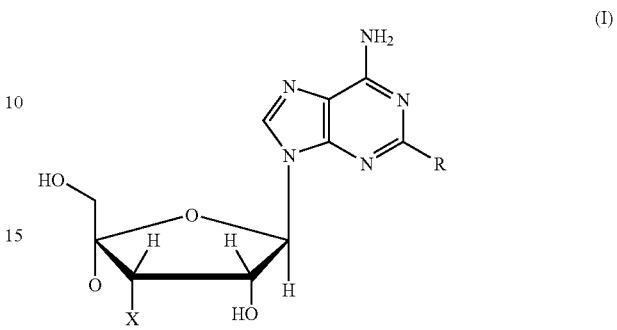

wherein R is $C_{1-4}$ alkoxy, and X is H or OH;
to a human subject in need of such treatment at a dosage which has been shown to give rise to a peak plasma concentration in a human test subject that is less than the $EC_{50}$ value of the compound at adenosine receptors at pH 7.4.

2. The method of claim 1, wherein the compound is administered to the human subject at a dosage that has been shown to result in a plasma concentration of the compound in a human test subject being maintained for more than 1 hour between one thousandth and one fifth of the $EC_{50}$ value of the compound at adenosine receptors at pH 7.4.

3. The method of claim 2 wherein the compound is 2-methoxyadenosine or a pharmaceutically acceptable salt thereof.

4. The method of claim 1, wherein the compound is administered to the human subject at a dosage that has been shown to result in a plasma concentration of the compound in a human test subject being maintained for more than 1 hour between one thousandth and one fifth of the minimum plasma concentration of the compound that gives has been shown to give rise to bradycardia, hypotension or tachycardia side effects in a human test subject.

5. The method of claim 1, wherein the compound is administered at a dosage of 0.2 to 1.2 mg/kg.

6. The method of claim 1, wherein X is OH.

7. The method of claim 6, wherein the compound is 2-methoxyadenosine, 2-ethoxyadenosine, or 2-butyloxyadenosine or a pharmaceutically acceptable salt thereof.

8. The method of claim 1, wherein X is H.

9. The method of claim 8, wherein the compound is 3'-deoxy-2-propoxyadenosine, 3'-deoxy-2-isopropoxyadenosine, or 3'-deoxy-2-butoxyadenosine or a pharmaceutically acceptable salt thereof.

10. The method of claim 1 wherein the compound is administered at a dosage of 0.1 to 2.0 mg/kg.

11. The method of claim 10 wherein the compound is 2-methoxyadenosine or a pharmaceutically acceptable salt thereof.

12. The method of claim 1 wherein the compound is administered at a dosage of 0.01 to 2.0 mg/kg.

13. The method of claim 12 wherein the compound is 2-methoxyadenosine or a pharmaceutically acceptable salt thereof.

14. The method of claim 1 wherein the compound is 2-methoxyadenosine or a pharmaceutically acceptable salt thereof.

* * * * *

UNITED STATES PATENT AND TRADEMARK OFFICE
CERTIFICATE OF CORRECTION

PATENT NO. : 7,790,698 B2  
APPLICATION NO. : 10/547454  
DATED : September 7, 2010  
INVENTOR(S) : Peter Richardson Page 1 of 2

It is certified that error appears in the above-identified patent and that said Letters Patent is hereby corrected as shown below:

On the Title page, column 2 (Other Publications), line 21, delete "methylisoquanosine" and insert -- methylisoguanosine --

On the Title page, column 2 (Abstract), line 9, delete "nH" and insert -- pH --

In column 8, line 7-19, in claim 1 delete " 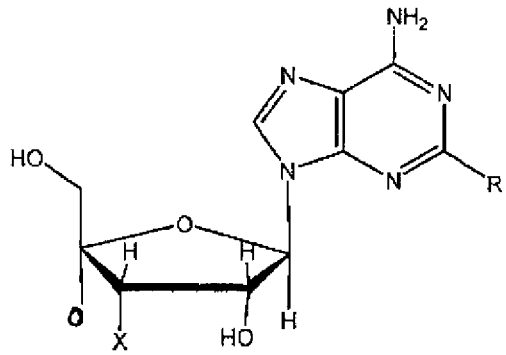 " and insert -- 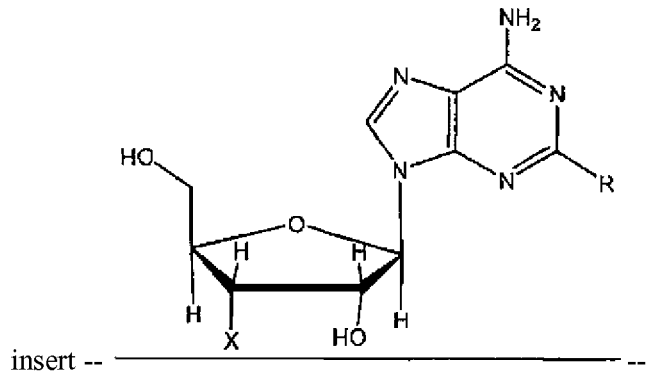 --

Signed and Sealed this  
Twenty-eighth Day of August, 2012

David J. Kappos  
*Director of the United States Patent and Trademark Office*

CERTIFICATE OF CORRECTION (continued)
U.S. Pat. No. 7,790,698 B2

In column 8, line 39, in claim 4, after "that" delete "gives"

In column 8, line 55, in claim 11, delete "claim 10" and insert -- claim 4 --

In column 8, line 60, in claim 13, delete "claim 12" and insert -- claim 5 --